United States Patent

Caisey et al.

[11] Patent Number: 5,598,843
[45] Date of Patent: Feb. 4, 1997

[54] COLORIMETRIC MEASUREMENT HEAD AND METHOD FOR DETERMINING THE INTERNAL COLOR OF A NON-OPAQUE MATERIAL

[75] Inventors: Laurence Caisey, Vitry-Sur-Seine; Daniel Bauer, Le Raincy, both of France

[73] Assignee: L'Oreal, Paris, France

[21] Appl. No.: 348,987

[22] Filed: Nov. 28, 1994

[30] Foreign Application Priority Data

Nov. 26, 1993 [FR] France ................................ 93 14165

[51] Int. Cl.⁶ .................................................. A61B 6/00
[52] U.S. Cl. ...................... 128/653.1; 128/665; 356/425; 356/445
[58] Field of Search ...................... 128/633, 634, 128/664–666, 653.1; 356/425, 445, 446, 448

[56] References Cited

U.S. PATENT DOCUMENTS

| | | | |
|---|---|---|---|
| 4,528,986 | 7/1985 | Arundel et al. | 128/665 |
| 4,810,875 | 3/1989 | Wyatt | 128/664 |
| 5,224,478 | 7/1993 | Sakai et al. | 128/666 |

FOREIGN PATENT DOCUMENTS

| | | | |
|---|---|---|---|
| 0019478 | 11/1980 | European Pat. Off. | 128/665 |
| 3137326 | 3/1983 | Germany | 128/665 |

*Primary Examiner*—Ruth S. Smith
*Attorney, Agent, or Firm*—Staas & Halsey

[57] ABSTRACT

A colorimetric measurement head, for determining the internal color of a non-opaque material, in particular the internal color of the human skin, includes an emitter which emits light, towards the material to be studied, and is separated by an opaque wall from a emitter which receives light which has penetrated into the material and which is reflected thereby. An external surface of the head, which is positioned at the material to be studied, and contacts this surface either by direct application against the surface, or with optical wetting. The light received by the detector comes from the interior of the material, whereas the light possibly reflected by the surface of the material or coming directly from the emitter cannot reach the detector because of the opaque separating wall.

10 Claims, 2 Drawing Sheets

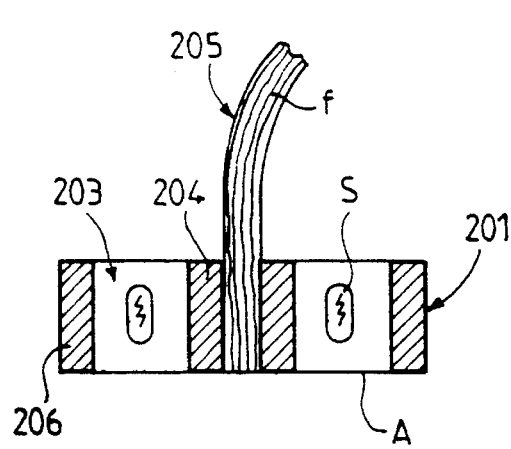
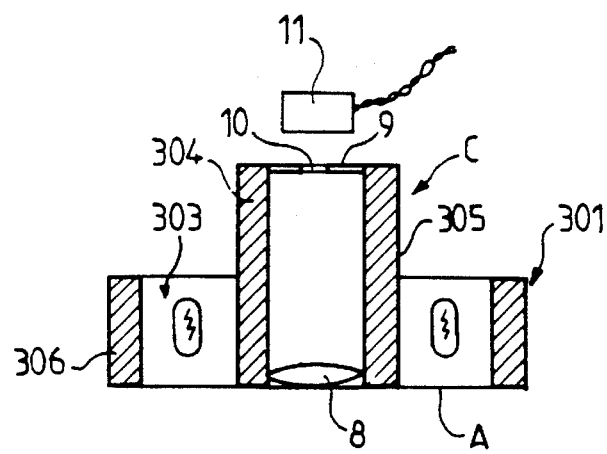
FIG. 6   FIG. 7
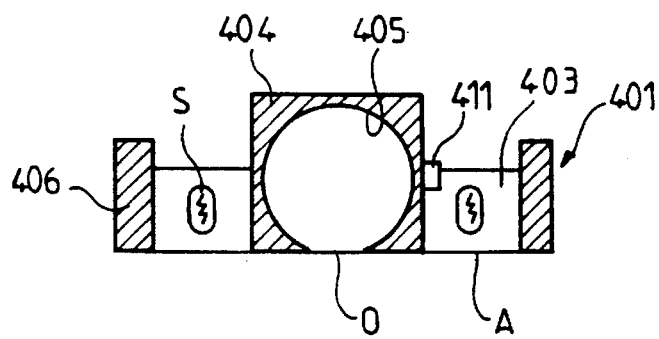
FIG. 8
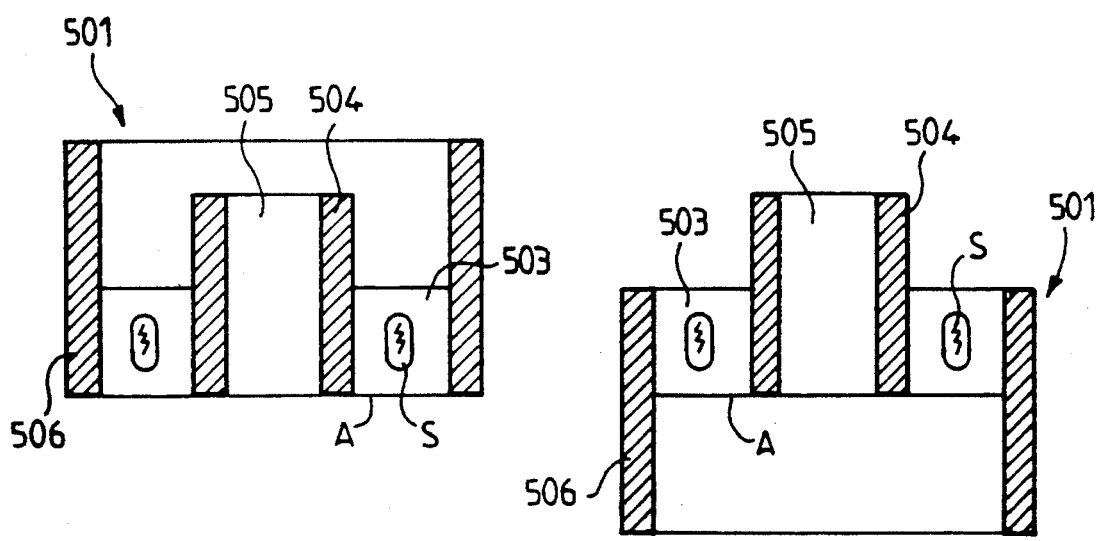
FIG. 9   FIG. 10

COLORIMETRIC MEASUREMENT HEAD AND METHOD FOR DETERMINING THE INTERNAL COLOR OF A NON-OPAQUE MATERIAL

BACKGROUND OF THE INVENTION

1. Field of the Invention

The invention relates to a colorimetric measurement head for determining the internal color of a non-opaque material, in particular the internal color of the human skin.

2. Description of the Related Art

Until now, the appearance of materials has been assessed with optical measurement apparatuses essentially making it possible to study the reflecting properties of the surface of these materials.

FR-A-2,650,890 relates to an optical apparatus intended to make it possible to evaluate the brilliance of a surface. This relatively complex apparatus involves polarizer and analyser filters. In addition, the measurement is carried out by eliminating the internal color component.

In all these optical devices, the light fluxes coming from the surface of the material to be studied are predictably good. These optical devices are therefore very useful for studying opaque surfaces.

In nature or in industry, however, objects exist which consist of materials which are complex from an optical point of view because at the same time, to a greater or lesser extent, they are transparent, selectively absorbent, scatter and are heterogeneous.

For such non-opaque materials, the information supplied by conventional optical measurement apparatuses does not allow the materials to be classified properly. In particular, these conventional measurement devices can give similar information, for two non-opaque materials of very different visual appearance, which does not make it possible to draw a distinction between the two materials.

SUMMARY OF THE INVENTION

The object of the invention is, above all, to provide a colorimetric measurement head which makes it possible to determine the internal color of a non-opaque material and, in particular, to make a distinction between two non-opaque materials of different visual appearance, for which, with a conventional colorimetric apparatus, no difference would be recorded.

A further object of the invention is to provide a colorimetric measurement head which has simple design, is economical and can essentially take into account the internal color component, without the brilliance component of the surface being involved.

According to the invention, a colorimetric measurement head, for determining the internal color of a non-opaque material, in particular the internal color of the human skin, includes an optical system which emits light towards the material to be studied and is separated by an opaque wall from an optical system which receives light which has penetrated into the material and which is reflected thereby. The external surface A of the head positioned at the material to be studied and contacts the surface of the material either by direct application against the surface of the material, or by an optical wetting. The head includes an outer opaque wall which slides between a projecting position for allowing conventional surface color measurement, and a retracted position in which the end of the opaque wall is located on the continuous surface of the end of the head, so as to be applied against the material and to allow measurement of the internal color of this non-opaque material.

With this colorimetric measurement head, the light received by the receiver comes from the interior of the material, whereas the light possibly reflected by the surface of the material or coming directly from the emitter cannot reach the receiver because of the opaque separating wall.

If this optical head is placed on an opaque surface, even one which is very white, no light is transmitted from the emitter to the detector. The same is true if the measurement head is placed on a perfectly transparent material.

This measurement head makes it possible to determine the quantity of light which passes into the material, especially into the skin, and which returns to the detector, by virtue of "optical conductors" formed by the material to be studied. It is thus possible to assess the "internal color" of the material and, in particular, to distinguish an "opaque, thick skin" from a "translucent skin".

The optical head is preferably surrounded by an opaque wall which protects the head against stray external light.

The optical head may have a cylindrical shape, preferably axisymmetric, the emitter and the receiver being coaxial and separated by an opaque coaxial cylindrical wall. An opaque outer wall surrounds the assembly.

The emitter may be designed to emit a parallel light beam or to emit diffuse light, with the aid of a diffusing glass placed in front of the light source, especially an annular flashlamp.

Similarly, the detector may provide either multidirectional detection or collimated detection.

The emitter and/or the detector may include an optical fibre, one end of which is located on the external surface of the head, intended to be applied against the material.

Collimated detection can be carried out with the aid of a system collimated with a converging lens and diaphragm at the focus of the lens, or a selective detection system with an optical fibre.

Multidirectional detection can be carried out with an integration sphere including an opening intended to be placed on the zone of the material to be studied, and a detection cell provided on the surface of the intregration sphere.

The detection system may be composed of trichromatic cells, a spectrophotometer or simply a photometer.

The invention also relates to a method for determining the internal color of a non-opaque material, wherein a colorimetric measurement head having a surface which matches the surface of the material is applied against this material, the measurement head including a light emitter separated from a receiver by an opaque wall.

The invention includes, apart from the arrangements described hereinabove, in a certain number of other arrangements which will be dealt with in more detail hereinbelow in conjunction with embodiments which are described with reference to the attached drawings but have no limiting character.

BRIEF DESCRIPTION OF THE DRAWINGS

FIG. 6 is a diagrammatic section of another variant with a receiver including an optical fibre.

FIG. 7 is a diagram of another variant with detection collimated with the aid of a converging lens.

FIG. 8 is a vertical axial section of a colorimetric measurement head variant with integration sphere at the level of the detector.

FIG. 9 is a diagrammatic section of an alternative embodiment of an optical head with a sliding opaque outer wall, in its retracted position.

FIG. 10, finally, shows, similarly to FIG. 9, the optical head when the opaque outer wall is projecting.

DESCRIPTION OF THE PREFERRED EMBODIMENTS

Figure 1:
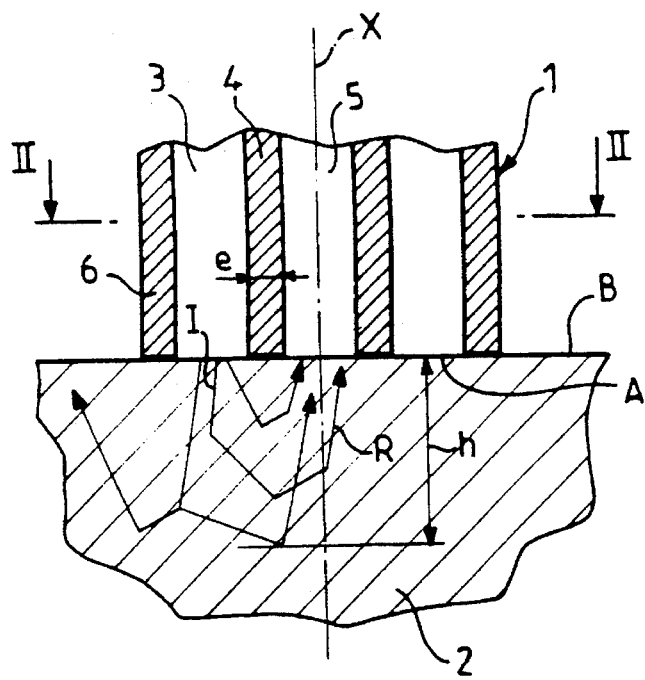
FIG. 1 of these drawings is a diagrammatic view in vertical axial section of a colorimetric measurement head according to the invention, applied against a non-opaque material to be studied.

Referring to FIG. 1, a colorimetric measurement head 1 can be seen, partially represented, which is for determining the internal color of a non-opaque material 2, in particular the human skin. The head 1 includes an optical system or emitter 3 which emits light towards the material 2 to be studied and is separated by an opaque wall 4 from an optical receiver system or detector 5.

In the example considered, the head 1 has the shape of a cylinder of revolution of vertical axis X. The emitter 3 has an annular shape, while the receiver 5 is arranged along the axis of the head 1. An opaque outer wall 6, also cylindrical, surrounds the emitter 3.

The emitter 3 includes an annular light source, which is not shown in FIG. 1 but is similar to the source S represented in FIG. 5 and described hereinbelow. An annular space contained between the light source and an end of the head 1 which is applied against the material 2 conducts light and can emit a parallel light beam or a diffuse light beam.

Figure 3:
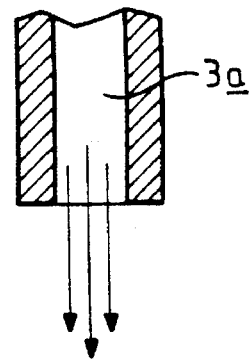
FIG. 3 is a simplified diagram of a light emitter producing directional emission.

In particular, the annular space of the emitter 3 may include a ring of optical fibres. FIG. 3 diagrammatically illustrates a fibre-optic parallel light emitter 3a.

Figure 4:
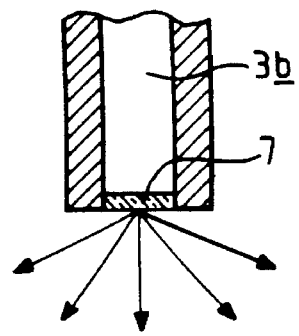
FIG. 4 is a diagrammatic section of a light emitter producing diffuse emission.

It is also possible to use an emitter 3b (FIG. 4) emitting diffuse light, for example with the aid of a diffusing glass 7 placed at the end of the emitter 3b which is turned towards the material to be studied.

The detector 5 may provide collimated detection, in parallel light, as will be explained in conjunction with FIGS. 6 and 7, or multidirectional detection. The detector 5 includes a photodetector element, not represented in FIG. 1, similar to the element 11 in FIG. 7 described hereinbelow.

An external surface A of the head 1 which is turned towards the material 2 to be studied is continuous and adapted to the surface B of the material so as to match this surface, either by direct application against the surface B, or with the interposition of a drop of oil or an equivalent.

In the example considered, the end surface A of the head 1 is plane and orthogonal to the axis X. It is clear that this end surface A might be curved, convex or concave, depending on the surface B of the material to be studied. The ends of the emitter 3, of the opaque wall 4, of the detector 5 and of the outer wall 6 are all in one and the same plane, so that, when the head 1 is applied against the surface B, as illustrated in FIG. 1, the incident light I coming from the emitter 3 cannot pass directly to the detector 5 because it is prevented from doing so by the wall 4. The detector 5 can collect only the light R which, after having penetrated into the material, is scattered and transmitted by this material, thereby defining types of "optical conductors".

The depth h to which it is possible for the emitted light which is subsequently collected by the detector 5 to enter into the material 2, depends on several factors, including the thickness e of the wall 4 separating the emitter 3 and detector 5. Increasing the thickness e causes, within certain limits, an increase in the depth h of the layers of the material which are included in the assessment of the color.

In practice, depending on the nature of the material and the depth to which it is designed to work, the thickness of the opaque separating wall 4 lies between 0.3 mm and 10 mm ($0.3 \leq e \leq 10$ mm).

It is naturally necessary to provide sufficient illumination, at the level of the emitter system 3, in order to include the relatively deep layers of the material 2.

Figure 2:
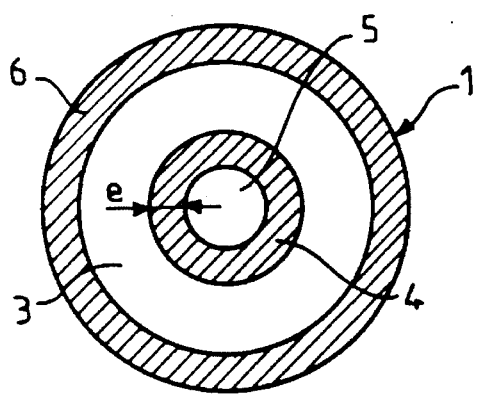
FIG. 2 is a section along II—II in FIG. 1.

The outer wall 6, which forms an opaque ring as shown in FIG. 2, limits the irradiated surface of the material 2 while providing protection against external stray light.

It is clear that it is possible to reverse the position of the emitter 3 and of the detector 5, with respect to the description given so far, that is to say that the emitter 3 may be located along the axis X of the head while the detector 5 may be annular.

Figure 5:
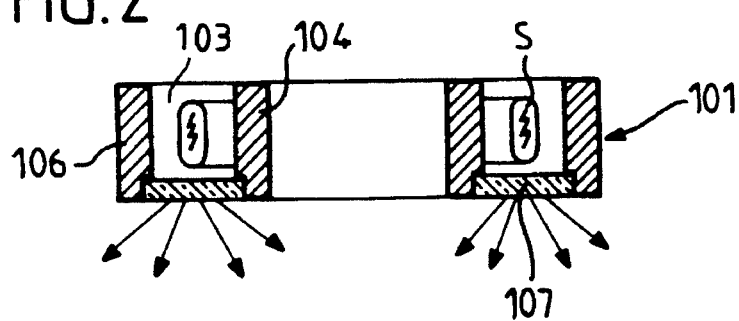
FIG. 5 is a vertical axial section of an alternative embodiment of the colorimetric measurement head.

FIG. 5 illustrates an alternative embodiment of the optical head 101 with diffuse emission. A light source S in the form of an annular flashlamp, concentric with the head 101, is arranged in the space contained between opaque walls 104, 106. A diffusing glass 107, in the form of a circular ring, is provided at the exterior surface of the head 101 which is intended to be applied against the material 2 to be studied.

FIG. 6 diagrammatically illustrates a head 201 in which the detector 205 includes an optical fibre f, the end of which is located in the plane of the surface A of the head 201 so as to be applied directly against the material 2 to be studied. The opening may be variable according to the optical fibre f. The optical fibre f makes it possible to produce collimated detection, which gives greater importance to the light coming from the depths of the material 2.

This collimated detection can be produced, as illustrated in FIG. 7, with the aid of a collimated system C in place of optical fibres. The system C includes, at the level of a detector 305, a converging lens 8 whose front face is in the plane of the surface A of the head 301 which is intended to be applied against the material 2. A cylinder 304 is also used whose length is equal to the focal length of the lens 8. A screen 9 with an aperture 10 at its center, located at the focus of the lens 8, is arranged at the end of the cylinder 304 which is remote from the lens 8. The photodetector 11 is placed behind the aperture 10, and receives a parallel light beam. The aperture 10 has a diameter commensurate with the quality of the collimation.

It should be noted that, without the lens 8, the cylinder 304 would constitute an integration chamber which makes it possible to collect the light without favoring a particular direction.

FIG. 8 illustrates an alternative embodiment of the optical head 401 with multidirectional detection by virtue of an integration sphere 405 provided at the level of the detector.

The separating wall 404 includes a kind of opaque block, inside of which a spherical cavity is made, the internal surface of which, constituting the integration sphere 405, is capable of reflecting the light. This surface is, for example, white. A circular opening O is provided at the bottom of the block 404 in order to make it possible for the light reflected by the material to be studied to enter the sphere 405. The plane of this opening O coincides with the plane A of the end of the head 401.

A detector 411 including either directly of a photodetector cell, or of the end of an optical fibre leading to a photodetector cell, or of any equivalent means, is provided in the block 404 in order to emerge at the surface of the sphere 405 and collect the light integrated by the sphere 405.

FIG. 9 illustrates an optical measurement head 501 variant according to the invention having "variable geometry". A central detector 505 surrounded by an opaque wall 504 is again seen. The emitter 503 is surrounded by a sliding opaque wall 506 whose axial length is greater than that of the detector 505.

In a retracted position represented in FIG. 9, the outer wall 506 has its lower end located in the plane A of the end of the head 501. In the configuration represented in FIG. 9, the head 501, being applied by its end A against the material 2 to be studied, makes it possible to determine the internal color of a non-opaque material.

By sliding the outer wall 506 downwards, as illustrated in FIG. 10, the end plane A of the emitter 503 and of the detector 505 is withdrawn with respect to the end of the outer wall 506 which will be applied against the material. In such a configuration, a colorimetric measurement of conventional type will be carried out, essentially relating to the surface color of the material.

The light source S can work with visible light, or in other ranges, for example in ultraviolet.

The optical head of the invention can be used for determining the internal color of a great variety of materials, other than skin, for example soaps, soap cakes, or fruit, such as apples, in particular in order to determine whether or not an apple is bruised, plastics, teeth, and any material which is not opaque or not perfectly transparent.

The light collected by the receiver system is analysed according to a conventional method, for example according to the L*, a*, b* colorimetric system.

L* (generally called brightness) denotes a measurement result which allows quantification from white to black (luminance).

a* is a measurement number which, if it is a high positive number, characterizes a highly red component.

a* highly negative characterizes a very green component.

b* is a measurement number which, if it is highly positive, characterizes a very yellow component.

b* highly negative characterizes a very blue component.

Conventional colorimetric analysis means were used with the measurement head according to the invention in order to analyse the light collected by the detector system 5. However, the three components given by these colorimetric analysis means no longer correspond exactly to the L*, a*, b* of the conventional system since the optical head was modified. T, α and β will be used to denote the three components obtained with a head according to the invention.

Measurements were carried out on two types of human skin, lying between very light and light, which had a different visual appearance.

A first series of measurements on these two skins was carried out with a conventional colorimeter manufactured by the company "Minolta" under the reference CR 200. The results obtained are as follows:

| L* | a* | b* |
|---|---|---|
| 70 | 6.2 | 16.6 |
| 70.1 | 6 | 16.5 |

Since the absolute uncertainty in the numerical values supplied by the equipment was of the order of ±0.3, it is seen that the values supplied for these two skins, having different visual appearance, by the conventional colorimeter, do not make it possible to distinguish between them.

With the colorimeter according to the invention, the following results were obtained:

| T | α | β |
|---|---|---|
| 34.8 | 29 | 40.8 |
| 31.6 | 27.1 | 37.9 |

On reading these numbers, it appears that, with the colorimeter according to the invention, a distinction is made between the two skins. Thus, according to the invention, it is possible to determine the internal color of a non-opaque material by applying against this material the colorimeteric measurement head which has a surface matching the surface of the material and which includes a light emitter separated from a detector by an opaque wall.

We claim:

1. Device for determining the surface and internal color of a non-opaque material, comprising:
    a colorimetric measurement head having
        an emitter including a light source which emits light towards the material,
        a detector which receives the light reflected by the material;
        a first opaque wall between the emitter and the detector; and
        a second opaque wall which is oriented outwardly of the emitter, detector and first opaque wall, and which is slidably mounted for movement between a projecting position wherein the first wall is spaced from the material and the second wall contacts the material to allow material surface color measurement, and a retracted position wherein both the first and second walls contact the material to allow measurement of the internal color of the non-opaque material.

2. Device according to claim 1, wherein the emitter comprises a parallel light beam emitter.

3. Device according to claim 1, wherein the emitter comprises a diffuse light emitter.

4. Device according to claim 1, wherein the detector comprises a multidirectional detector.

5. Device according to claim 4, wherein the detector comprises an integration sphere.

6. Device according to claim 1, wherein the detector comprises a collimated detector.

7. Device according to claim 6, wherein the detector comprises:
    a converging lens, a front face of which is located at an external surface of the head, a screen arranged with an aperture at the center thereof located at a focus of the lens, and a photodetector placed behind the aperture.

8. Device according to claim 1, further comprising fluid located between and contacting the head and the material.

9. Method for determining the surface and internal color of a non-opaque material, comprising the steps of:

providing a colorimetric measurement head including a light emitter, a light detector, a first opaque wall separating the emitter and detector, and a second opaque wall which is oriented outwardly of the emitter, detector and first opaque wall, and which is slidably mounted for movement between a projecting position wherein the first wall is spaced from the material and the second wall contacts the material, and a retracted position wherein both the first and second walls contact the material;

placing the second wall in the retracted position;

emitting light from the emitter into the material;

detecting the light penetrating the material and reflected thereby using the light detector for allowing measurement of the internal color of the non-opaque material;

placing the second wall in the projecting position;

emitting light from the emitter toward the material; and detecting the light reflecting from the surface of the material for allowing measurement of the surface color of the non-opaque material.

10. The method as recited in claim 9, further comprising the step of contacting the head with the material with optical wetting.

* * * * *